United States Patent [19]
Vaillancourt

[11] Patent Number: 5,100,389
[45] Date of Patent: Mar. 31, 1992

[54] AMBULATORY INFUSION PUMP

[76] Inventor: Vincent L. Vaillancourt, 14 Bunyan Dr., Livingston, N.J.

[21] Appl. No.: 642,175

[22] Filed: Jan. 17, 1991

Related U.S. Application Data

[63] Continuation of Ser. No. 209,514, Jun. 21, 1988, abandoned.

[51] Int. Cl.⁵ ............................................. A61M 5/20
[52] U.S. Cl. .................................. 604/135; 604/246
[58] Field of Search ........ 604/118, 126, 131, 134–137, 604/157, 190, 207, 222, 230, 236, 246, 249, 250, 252; 128/DIG. 12

[56] References Cited

U.S. PATENT DOCUMENTS

| | | | |
|---|---|---|---|
| 1,633,293 | 6/1927 | Smiley | 604/135 |
| 1,835,122 | 12/1931 | Thevenot | 604/135 |
| 2,221,739 | 10/1939 | Reiter | 604/135 |
| 2,590,138 | 3/1952 | Willis | 604/135 |
| 2,954,767 | 12/1957 | Rane | 604/222 |
| 3,245,591 | 4/1966 | Kneusel et al. | 222/389 |
| 3,334,788 | 8/1967 | Hamilton | 604/135 |
| 3,451,393 | 1/1969 | Sarnoff | 604/135 |
| 3,831,602 | 8/1974 | Broadwin | 604/186 |
| 4,400,277 | 8/1983 | Leason | 604/252 |
| 4,813,937 | 3/1989 | Vaillancourt | 604/135 |
| 4,874,386 | 10/1989 | O'Boyle | 604/135 |

*Primary Examiner*—John D. Yasko
*Assistant Examiner*—Anthony Gutowski
*Attorney, Agent, or Firm*—Wyatt, Gerber, Burke & Badie

[57] ABSTRACT

The ambulatory infusion pump is provided with a preloaded spring having a fixed spring constant. A tab is provided to release the preloaded spring to impose a biasing force on the piston of the pump. The piston slides within the housing against a substantially constant friction force when moving from the filled position toward the empty position. The biasing force of the spring and the stroke of the piston are coordinated so as to maintain a pressure on the fluid being dispensed from the pump housing which decreases at a slow rate and within a range of about 15% of the referenced pressure.

22 Claims, 2 Drawing Sheets

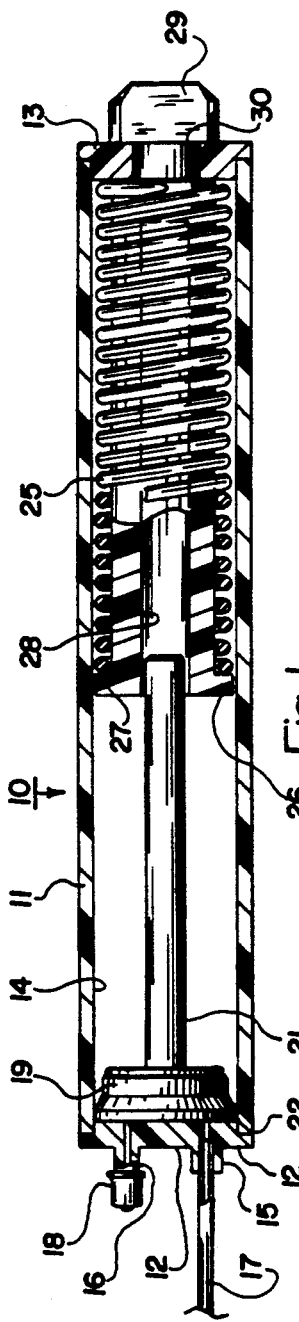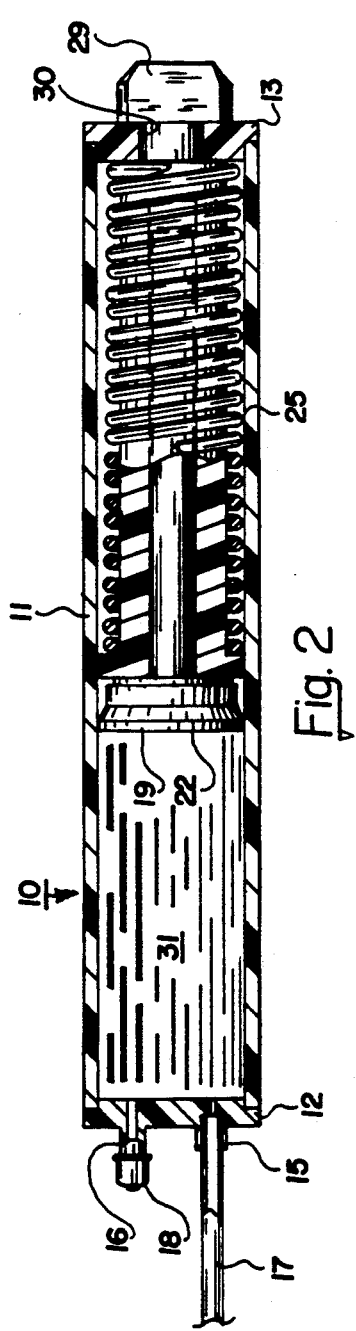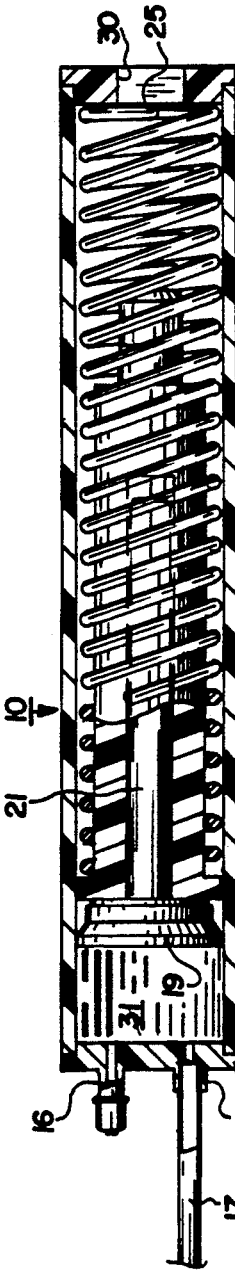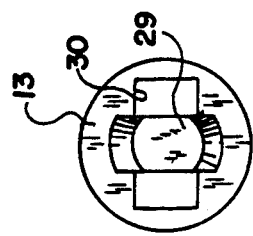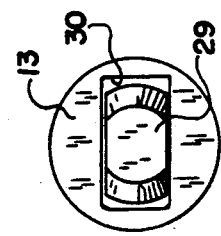

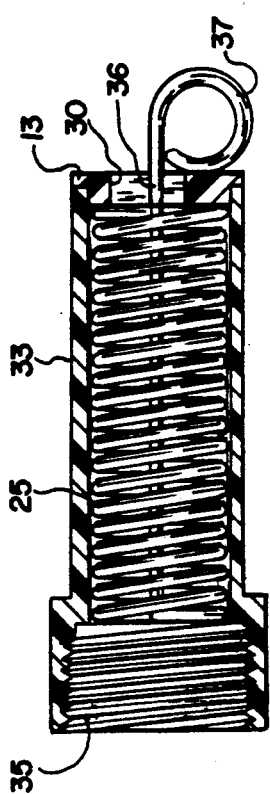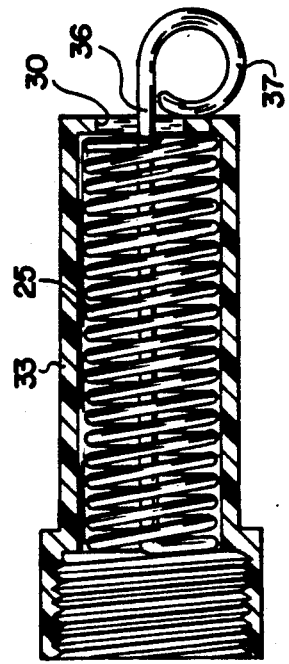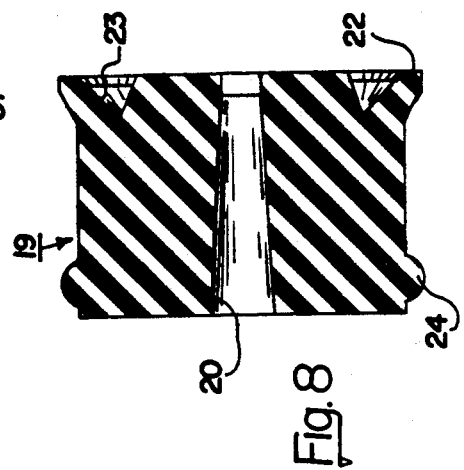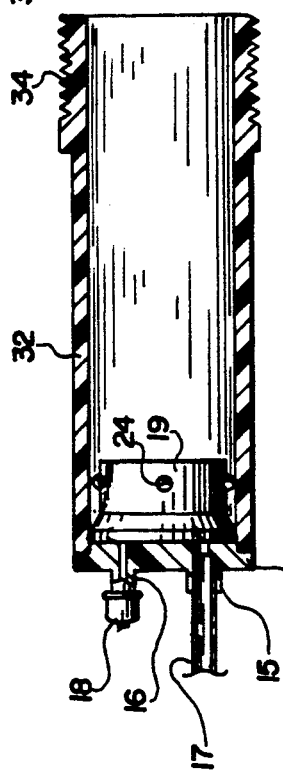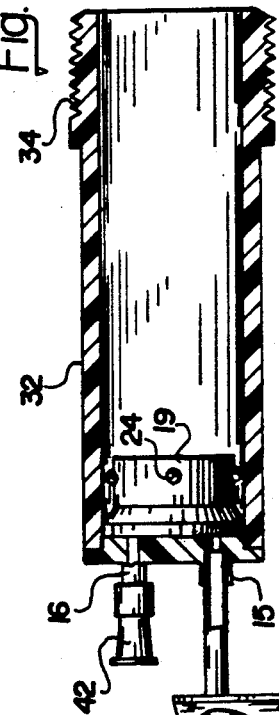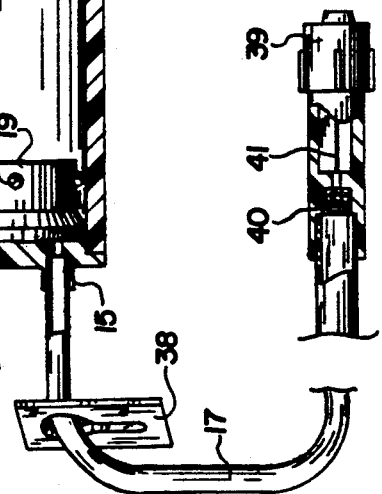
Fig. 6  Fig. 7  Fig. 8

AMBULATORY INFUSION PUMP

This application is a continuation, of application Ser. No. 07/209,514, filed June 21, 1988, now abandoned.

This invention relates to an ambulatory infusion pump. More particularly, this invention relates to an ambulatory infusion pump for dispensing fluids such as medications.

Heretofore, various types of devices have been known for dispensing drugs in liquid form to a patient. In some cases, for example as described in U.S. Pat. Nos. 4,386,929 and 4,265,241 use has been made of inflated bladders or bellows to dispense a liquid upon deflation of the bladder or collapse of the bellows. However, such devices have been relatively expensive to construct and generally are not capable of dispensing a fluid at a constant pressure particularly as the bladder or bellows approaches an empty condition. Further, there is a risk that a bladder may rupture prior to or during use. Still further, since a bladder cannot completely collapse, residual amounts of fluid may remain in the device without being discharged into a patient. Hence, either the device must be charged with an excess amount of fluid medication or the device must be discarded with residual fluid medication. In either case, a needless expense arises in terms of unused fluid medication and actual costs.

Infusion devices have also been known, such as described in U.S. Pat. Nos. 4,414,983 and 4,636,197 wherein reliance is made upon a resilient strap or endless band for driving a syringe plunger into a syringe housing in order to expel fluid from the housing. However, since the resilient straps and endless bands are exposed, these elements are subject to external forces which may dislodge, impair or rupture the straps or bands during transportation or use.

Devices have also been known for injecting fluids which use springs, such as described in U.S. Pat. No. 3,530,785. However, such devices employ the spring to close off a valve rather than for providing a metering of the fluid injected.

Further, infusion pumps have been known which employ constant force springs to impose a driving force on a piston in order to expel fluid from a housing. However, such constant force springs are relatively expensive and generally do not lend themselves to being considered for single patient use. Still further, such pumps tend to have a limited piston stroke available for any given pump size thus leading to limited capacities.

Accordingly, it is an object of the invention to provide an infusion pump of relatively simple construction.

It is another object of the invention to provide an infusion pump which is able to maintain a substantially uniform rate of discharge of fluid over time.

It is another object of the invention to provide an infusion pump which can be readily manufactured in an inexpensive manner.

It is another object of the invention to provide an infusion pump which can be worn by a patient and used in a reliable manner.

It is another object of the invention to be able to change the flow rate of an infusion pump.

Briefly, the invention provides an infusion pump which is able to deliver fluid over a prolonged period of time at a pressure which changes by less than about plus or minus 15% of the referenced pressure over the total time period. To this end, the infusion pump is comprised of a tubular housing for a fluid, a piston slidably mounted in the housing and a spring within the housing for imposing a biasing force on the piston which decreases during movement of the piston from a filled position to an empty position.

The tubular housing is provided with an outlet aperture at the distal end for the fluid as well as with an injection portion for injection of fluid into a fluid-receiving chamber between the piston and distal end of the housing.

The piston is slidably mounted in the housing to move from the filled position to the empty position with a substantially constant friction force between the piston and the housing.

The spring within the housing for imposing the biasing force is in the form of a helical spring having a spring constant, for example of 1.5 pounds per inch or less. The spring is also mounted in a preloaded condition within the housing of the pump and is provided with a means for releasing the spring to impose a force on the piston.

The infusion pump is constructed to discharge fluid over a prolonged period of time with a minimal decrease in fluid pressure so as to obtain an infusion rate which varies by no more than about plus or minus 15% from the beginning to end of the time period. To this end, the housing is provided with a cylindrical barrel of an inside diameter of one inch (2.54 centimeters) or less while the helical spring is sized with a constant of 2 pounds per inch or less and is disposed to have a stroke of about two inches (5.08 centimeters).

When in operation, this spring which is preloaded will initially impose a force on the fluid in the barrel of the housing via the piston which is reduced by the friction force between the piston and the housing. As fluid is infused into a patient, the spring will slowly elongate so that the spring force decreases while the friction forces remain constant or substantially constant. However, since the spring constant and the stroke can be readily selected, the decrease in the spring force and thus the pressure on the fluid can be kept to a minimal range, for example, within about plus or minus 15% of the initial pressure, from beginning to end of the stroke.

In the case of housings having large diameter barrels or bores, for example, of two inches (5.08 centimeters), or more, the friction force between the piston and the housing increases substantially For example, for a two inch piston commonly used in an infusion pump, the friction force may total between six and eight pounds as compared to a three pound friction force for a one inch diameter piston.

In addition, a restrictor element, for example, having a flow diameter of 0.005 inches or less, is positioned in a conduit extending from the outlet aperture and cooperates with the spring to produce a flow which varies in output over the stroke of the piston of less than about plus or minus 15%.

In one embodiment, the helical spring may cooperate with a sleeve which is slidably mounted within the housing for biasing the piston towards the distal end of the housing. In this case, the piston may also be provided with a shaft which is slidably received within the sleeve.

In another embodiment, the housing may be made of two sections which are releasably secured to each other. In this case, the distal housing section may contain the piston while the proximal housing section houses the spring. In addition, the two sections may be threadably secured to each other so that the proximal section can be removed and replaced with another similar housing section containing a spring with a different spring constant.

In the case of large size bores, for example, of 1¼ inches or more, provisions may be made for a decreasing friction force between the piston and the housing, for example, the housing may be provided with an inner bore of increasing diameter towards the distal end while the piston is provided with a resilient annular portion at the distal end for sealingly engaging with the housing within the inner bore. Further, the piston may be provided with circumferentially disposed protuberances for guiding the piston within the housing. In this case, as the spring force decreases during the piston stroke, the friction force also decreases so that the fluid pressure decreases at a slower rate than the spring force decrease.

In use, after filling of the fluid chamber of the pump with fluid, pressure may be applied to the piston. At this time, the piston will be slightly compressed due to the pressure of the spring on one side and the pressure on the fluid on the opposite side. The friction force between the piston and the housing will thus slightly increase. Once fluid begins to flow from the chamber, that is, upon opening of the restrictor, the pressure of the fluid will decrease substantially linearly within a relatively small range until emptying of the fluid chamber. In this respect, the spring biasing force on the piston gradually decreases as the piston moves towards the distal end of the housing while the friction force between the piston and the housing remains substantially constant since the rate of piston movement is relatively slow. Thus, the overall fluid pressure decreases relatively slowly and remains within about a 15% range of the initial pressure.

The infusion pump may be operated so as to achieve a maximum accuracy in flow rate of between plus or minus 10% and 15%. For example, a maximum pressure variation of 2 psi can be maintained between the full and empty conditions for a starting pressure of 6 psi. In like manner, a variation of 3 psi can be maintained if the starting pressure is 10 psi, and so forth. Thus, when starting from the full position, the pump may deliver fluid at a higher pressure than a nominal pressure while at the empty position, the pump is delivering at a pressure less than the nominal pressure.

In constructing the pump, once a reservoir capacity is established, for example in chemotherapy, a 50 cubic centimeter capacity can be established. The size of the housing bore or barrel diameter is then optimized, that is, made as small as possible in order to achieve the accuracy required. With the barrel diameter optimized in conjunction with the piston stroke length, a length of spring having a spring constant of 1.5 pounds per inch or less is then selected so as to provide the appropriate preloading force, taking into account the friction force between the piston and housing.

The infusion pump may be carried about in a coat pocket or strapped to a patient's body for infusion purposes.

These and other objects and advantages of the invention will become more apparent from the following detailed description taken in conjunction with the accompanying drawings wherein:

FIG. 1 illustrates a cross sectional view of an infusion pump constructed in accordance with the invention in an empty condition;

FIG. 2 illustrates a view of the infusion pump of FIG. 1 in a filled condition;

FIG. 3 illustrates a cross sectional view of the pump of FIG. 1 in an intermediate dispensing condition;

FIG. 4 illustrates a proximal end view of the infusion pump of FIG. 1 in a locked condition;

FIG. 5 illustrates a proximal end view of the infusion pump in an unlocked position;

FIG. 6 illustrates an exploded view of a modified infusion pump in accordance with the invention;

FIG. 7 illustrates a modified infusion pump constructed in accordance with the invention: and FIG. 8 illustrates a cross sectional view of a piston constructed in accordance with the invention.

Referring to FIG. 1, the infusion pump is constructed for use as an ambulatory infusion pump, for example for dispensing fluid medication into a patient.

The infusion pump 10 includes a tubular housing 11, for example made of plastic. As indicated, the housing 11 is formed of a cylindrical barrel having end caps 12, 13 at the respective ends and has an inner bore 14 which is of uniform diameter for example, of one inch inside diameter. The distal end cap 12 is provided with an outlet aperture 15 for fluid as well as an injection port 16 for injection of fluid into the housing. The outlet aperture 15 may be connected with a conduit 17 for the dispensing of fluid while the injection port 16 is provided with a removable cover 18.

The infusion pump 10 also includes a piston 19 which is slidably mounted in the housing 11 to move from a filled position as illustrated in FIG. 2 to the empty position illustrated in FIG. 1, i.e. to the distal end, while defining a fluid-receiving chamber with the distal end of the housing 11.

Referring to FIG. 8, the piston 19 is formed as a rubber plug or block of cylindrical shape having a central bore 20 for receiving a mounting shaft 21 as indicated in FIG. 1. In addition, the piston 19 has a resilient annular portion 22 at the distal end for sealingly engaging the housing 11 within the inner bore. As illustrated, the annular portion 22 is formed so as to be biased radially outwardly. For example, the distal face of the piston 19 is provided with an annular groove 23 of V-shape in order to form the annular portion 22. Of note, where the piston 19 is not to be mounted on the shaft 21, the piston 19 is provided with circumferentially disposed protuberances 24 towards the distal end which are provided for guiding the piston 19 within the housing 11 (see FIG. 6).

Referring to FIG. 1, the pump 10 also includes a means in the form of a preloaded helical spring 25 within a proximal end of the housing 11 for imposing a biasing force on the piston 19 in a direction towards the distal end of the housing 11 which decreases during movement of the piston 19 from the filled position (FIG. 2) to the empty position (FIG. 1). In this regard, the helical spring 25 has a spring constant, for example of 1.5 pounds per inch or less.

The spring constant is coordinated with the size and stroke piston 19 in the housing 11 to maintain a pressure on the fluid in the chamber between the piston 19 and the distal end of the housing 11 which decreases substantially linearly within a relatively small range. For example, the housing 11 may have an inside diameter of one inch, the piston 19 may have a stroke of two inches and the spring 25 may have a spring constant of one pound per inch which being preloaded to impose a fourteen pound force on the piston 19 in the filled position. In this case, assuming the friction force between this piston 19 and housing 11 is three pounds, the net biasing force of the fluid is of eleven pounds imposing a pressure of 14.0 psi. As the spring 25 elongates to the empty position, i.e. over a two inch stroke, the biasing force reduces to nine pounds and the fluid pressure to 11.45 psi. Such a pump has a fluid volume which is infused with about 25.75 cubic centimeters.

Thus, by establishing a nominal pressure between the initial delivery pressure and final pressure, the pump may operate within a range of ten percent (10%) of the nominal pressure. For example, for the above example, a nominal pressure of 12.75 psi may be used.

As shown in FIG. 1, a sleeve 26 is slidably mounted in a proximal end of the housing 11 with the spring 25 coiled about the sleeve 26. In this respect, the distal end of the sleeve 26 has a radial flange 27 against which the spring 25 abuts. The proximal end of the spring 25 abuts against the proximal end cap 13 of the housing 11. The sleeve 26 also has an internal bore 28 which slidably receives the mounting shaft 21 of the piston 19. As indicated, the sleeve 26 is closed at the proximal end and provides an abutment for the proximal end of the shaft 21 when the piston 19 is in the filled position (FIG. 2).

The spring 25 is mounted in a preloaded condition and is provided with a means for releasing the spring 25 from the preloaded state. For example, this means includes a tab 29 which is secured to a proximal end of the sleeve 26 and which is sized to selectively pass through a slot 30 in the end cap 13 of the housing 11. As indicated in FIG. 4, the slot 30 is of rectanqular shape while the tab 29 is of similar rectangular shape. When turned from the position illustrated in FIG. 4 to the position illustrated in FIG. 5, wherein like references characters indicate like parts as above, the tab 29 is able to slide through the slot 30 to release the spring 25 from the preloaded condition.

Referring to FIG. 3, once the spring 25 has been released, the spring 25 biases the sleeve 26 against the piston 19 and thus biases the piston 19 towards the distal end of the housing 11 in order to impose a sufficient pressure on fluid within the fluid chamber 31 of the pump 10 to expel the fluid.

As indicated in FIG. 1, the proximal end cap 13 serves as a mount for the preloaded spring 25 and sleeve 26. Thus, these elements may be removed from the housing 11 should a need arise to change the spring 25 for a spring having a different spring constant.

Referring to FIG. 6, wherein like reference characters indicate like parts as above, the pump 10, may have a housing formed of a pair of tubular sections 32, 33 which are removably secured together in coaxial relation. In addition, the distal section 32 may contain the piston 19 while the proximal section 33 contains the spring 25. The distal section 32 may also be provided with an external thread 34 to threadably receive an internal thread 35 on the other section 33. Thus, the proximal housing section 33 may be removed and replaced by a similar housing section with a spring having a different spring constant. As indicated in FIG. 6, the housing sections 32, 33 may each be made of plastic. Alternatively, as indicated in FIG. 7, wherein like references indicate like parts as above, the proximal housing section 33' may be made of a metal such as aluminum.

Referring to FIG. 6, the means for releasing the spring 25 from the preloaded condition may be in the form of a rod 36 secured to a distal end of the spring 25 and extending through the slot 30 in the end cap 13 of the housing section 33 while a handle 37 in the form of a loop is provided at the proximal end of the rod 36 for selective passage through the slot 30 upon rotation. When the handle 37 is in the position illustrated in FIG. 6, the spring 25 remains in a preloaded condition. When the handle 37 is turned 90°, the handle 37 then passes through the slot 30 in the end cap 13 so that the spring expands to impose a biasing force on the piston 19 when in the filled position.

Referring to FIG. 7, the conduit may be provided with a clamp of known construction and purpose as well as with a restrictor 39 for dispensing of fluid at a predetermined rate. Such a restrictor 39, as known, may be provided with a filter 40 for filtering the liquid flow and a see-through chamber 41 for viewing of fluid therein.

Referring to FIG. 1, in order to use the infusion pump 10, a suitable injection means is provided for passing fluid through the injection port 16 into the housing 11. At this time, the injection pressure of the fluid causes the piston 19 to slide in the proximal direction while the shaft 21 slides into the sleeve 26. During this time, relatively little pressure is required in order to move the piston 19. When the piston has achieved the filled position, for example, as shown in FIG. 2, and the pump 10 is otherwise connected in place and is ready for use, the tab 29 is rotated from the position shown in FIG. 4 to the position shown in FIG. 5 to release the preloaded spring 25. The spring then presses the sleeve 26 against the piston 19 to impose a biasing force on the piston 19 and thus impose a pressure on the fluid in the fluid chamber 31. At the same time, the piston 19 is slightly compressed axially by the force of the spring 25 and the pressure of the fluid in the pressure chamber 31. In addition, the annular portion 22 (see FIG. 8) of the piston 19 is biased radially outwardly under a slightly greater force. As the spring 25 expands, fluid is forced out of the chamber 31 to the conduit 17 to pass into and through the restrictor (see FIG. 7). As the fluid is dispensed over time, the spring 25 continues to expand. During this time, the biasing force of the piston decreases in accordance with the spring constant. At the same time, the friction force between the piston 19 and the housing 11 remains the same or substantially so. Preferably, the stroke of the piston is matched to the decrease in spring biasing force so that a pressure is imposed on the fluid in the chamber 31 which decreases substantially linearly at a low rate until the piston 19 comes into the empty position (FIG. 1). By way of example, the springs which are used in the infusion pump 10 are capable of generating pressure of from 6 psi to 15 psi or higher as required.

By appropriate choice of restrictor, housing diameter and biasing force, the continuous flow rate of the fluid from the pump may be in the range of one cubic centimeter to five cubic centimeters per hour. Other flow rates may be obtained by either increasing or decreasing the size of a discharge orifice restrictor.

The flow rate may also be changed by changing the spring. For example, for a restrictor having a one-half inch length orifice with an opening of 0.0018 inch diameter, a spring having an internal force of 15 pounds and a spring constant of one-pound per inch may be replaced by a 12 pound spring having the same spring constant. In the first case, the flow rate is 3 cubic centimeters per hour while in the latter case, the flow rate decreases to 2.3 cubic centimeters per hour.

In constructing the infusion pump, the piston is constructed to have a limited stroke for a given pump size. Further, if the starting pressure is 6 psi, the maximum pressure variation between the filled condition and the empty condition should be no more than 2 psi. If the starting pressure is 10 psi, the maximum pressure variation should be no than 3 psi, and so forth. The actual pressure (force) delivered to the fluid is the biasing pressure less the friction pressure due to the spring (very small) and less the friction force between the piston and housing which can be substantial.

For larger infusion pumps, for example, having a bore of two inches, and a capacity of about 100 cubic centimeters for a two inch stroke, the bore can be made with an increasing diameter towards the distal end to reduce the friction force on the piston and thus reduce the rate of pressure decrease on the fluid.

Further, valves such as a one-way valve 42 may be connected with the injection port 16 instead of a cover.

The invention thus provides an infusion pump which can deliver fluid over a prolonged period of time with a minimal change in pressure. In addition, the invention provides an infusion pump which can be made in a relatively simple and inexpensive manner without need for expensive springs.

The invention this provides an infusion pump which can be made of compact construction so as to be readily carried in a coat pocket or strapped to a body. Further, the pump is not subject to degradation due to ultraviolet radiation or normal warehousing conditions.

The infusion pump is intended for one time use and is disposable.

What is claimed is;

1. An ambulatory infusion pump comprising
   a tubular housing for a fluid having an outlet aperture at a distal end for dispensing fluid into a conduit and an inner bore of predetermined diameter;
   a piston slidably mounted in said housing between a filled position and an empty position at said distal end to define a fluid-receiving chamber with said distal end;
   a preloaded helical spring in said housing for imposing a decreasing biasing force on said piston to move said discharge fluid from said chamber and to maintain a decreasing pressure on the fluid in said chamber which varies no more than 15% of a nominal pressure during movement of said piston from said filled position to said empty position while effecting a continuous flow rate in the range of from 1 cc to 5 cc per hour;
   a sleeve slidably mounted in a proximal end of said housing with said spring coiled about said sleeve for biasing said sleeve against said piston and toward said distal end of said housing; and
   means for releasing said spring to impose said force on said piston.

2. An infusion pump as set forth in claim 1 wherein said spring has a spring constant of no ore than 2.0 pounds per inch.

3. An infusion pump as set forth in claim 1 wherein said spring has a spring constant of 1.5 pounds per inch.

4. An infusion pump as set forth in claim 3 wherein said housing has an inner bore of a diameter of one inch.

5. An ambulatory infusion pump as set forth in claim 1 wherein said piston has a resilient annular portion at a distal end sealingly engaging said housing within said inner bore.

6. An ambulatory infusion pump as set forth in claim 5 wherein said annular portion is biased radially outwardly.

7. An ambulatory infusion pump as set forth in claim 5 wherein said piston includes circumferentially disposed protuberances for guiding said piston within said housing.

8. An ambulatory infusion pump as set forth in claim 1 which further comprises a shaft secured to said piston and slidably received in said sleeve.

9. An ambulatory infusion pump as set forth in claim 1 wherein said means includes a tab secured to a proximal end of said sleeve and sized to selectively pass through a slot in a proximal end of said housing upon rotation of said tab.

10. An ambulatory infusion pump as set forth in claim 1 wherein said housing has an injection port at said distal end for injection of fluid into said chamber.

11. An ambulatory infusion pump as set forth in claim 1 wherein said housing includes a pair of tubular sections removably secured together in coaxial relation, one of said sections having said piston slidably mounted therein and the other of said sections having said spring mounted therein.

12. An ambulatory infusion pump as set forth in claim 11 wherein said one housing section is made of plastic of said other housing section is made of metal.

13. An ambulatory infusion pump as set forth in claim 1 wherein said means includes a slot at a proximal end of said housing, a rod secured to a distal end of said spring and extending through said slot and a handle secured to a proximal end of said rod for selective passage through said slot upon rotation of said handle.

14. An ambulatory infusion pump as set forth in claim 1 which further comprises a conduit connected to said outlet aperture a restrictor at a distal end of said conduit for discharging fluid therefrom and a filter in said conduit upstream of said restrictor.

15. An ambulatory infusion pump as set forth in claim 1 wherein said housing bore has a diameter of not more than 1 inch and said spring has a spring constant of not more than 1.5 pounds per inch.

16. An ambulatory infusion pump as set forth in claim 15 wherein said piston has a stroke of 2 inches between said filled position and said empty position.

17. An ambulatory infusion pump as set forth in claim 16 wherein said spring has a spring constant of 1 pound per inch.

18. An ambulatory infusion pump as set forth in claim 1 wherein said bore has a diameter which increases in a direction towards said outlet aperture from said filled position to permit a decrease in friction force between said piston and said housing as said piston moves toward said empty position.

19. An ambulatory infusion pump as set forth in claim 18 wherein said bore has a diameter of 2 inches at said filled position.

20. An ambulatory infusion pump comprising
    a tubular housing for a fluid having an outlet aperture at a distal end for dispensing fluid into a conduit and an inner bore of predetermined diameter;
    a piston slidably mounted in said housing between a filled position and an empty position at said distal end to define a fluid-receiving chamber with said distal end;
    a preloaded helical spring in said housing for imposing a decreasing biasing force on said piston to move said fluid from said chamber to maintain a pressure on the fluid in said chamber which varied no more than 15% of a nominal pressure during movement of said piston from said filled position to said empty position;

means for releasing said spring to impose said force on said piston;

a sleeve slidably mounted in a proximal end of said housing with said spring coiled about said sleeve for biasing said sleeve against said piston and toward said distal end of said housing; and a shaft secured to said piston and slidably received in said sleeve.

21. An ambulatory infusion pump comprising a tubular housing for a fluid having an outlet aperture at a distal end for dispensing fluid into a conduit and an inner bore of predetermined diameter;

a piston slidably mounted in said housing between a filled position and an empty position at said distal end to define a fluid-receiving chamber with said distal end;

said bore having a diameter which increases in a direction towards said outlet aperture from said filled position to permit a decrease in friction force between said piston and said housing as said piston moves toward said empty position;

a preloaded helical spring in said housing for imposing a decreasing biasing force on said piston to move said discharge fluid from said chamber to maintain a pressure on the fluid in said chamber which varies no more than 15% of a nominal pressure during movement of said piston from said filled position to said empty position; and means for releasing said spring to impose said force on said piston.

22. An ambulatory infusion pump as set forth in claim 21 wherein said bore has a diameter of 2 inches at said filled position.

* * * * *

UNITED STATES PATENT AND TRADEMARK OFFICE
CERTIFICATE OF CORRECTION

PATENT NO. : 5,100,389

DATED : March 31, 1992

INVENTOR(S) : Vincent L. Vaillancourt

It is certified that error appears in the above-identified patent and that said Letters Patent is hereby corrected as shown below:

```
Column 2, line 29 after "with a" insert -spring-
Column 4, line 60 after "stroke" insert -of the-
Line 67 change "which" to -while-
Column 7, line 59 change "ore" to -more-
Column 9, line 1 change "varied" to -varies-
```

Signed and Sealed this

Seventeenth Day of August, 1993

Attest:

BRUCE LEHMAN

Attesting Officer

Commissioner of Patents and Trademarks